US010058245B2

(12) United States Patent
Herranen et al.

(10) Patent No.: US 10,058,245 B2
(45) Date of Patent: Aug. 28, 2018

(54) OPTOMETRIC INSTRUMENT WITH ALIGNMENT MEANS AND METHOD FOR ALIGNING AN OPTOMETRIC INSTRUMENT

(71) Applicant: ICARE FINLAND OY, Vantaa (FI)

(72) Inventors: Teemu Herranen, Hyvinkää (FI); Ari Kukkonen, Helsinki (FI)

(73) Assignee: ICARE FINLAND OY, Vantaa (FI)

(*) Notice: Subject to any disclaimer, the term of this patent is extended or adjusted under 35 U.S.C. 154(b) by 214 days.

(21) Appl. No.: 14/973,988

(22) Filed: Dec. 18, 2015

(65) Prior Publication Data

US 2016/0174838 A1 Jun. 23, 2016

Related U.S. Application Data

(63) Continuation of application No. PCT/FI2014/050500, filed on Jun. 19, 2014.

(30) Foreign Application Priority Data

Jun. 20, 2013 (FI) ..................................... 20135684
Aug. 30, 2013 (FI) ..................................... 20135876

(51) Int. Cl.
*A61B 3/10* (2006.01)
*A61B 3/12* (2006.01)
(Continued)

(52) U.S. Cl.
CPC ................ *A61B 3/12* (2013.01); *A61B 3/152* (2013.01); *A61B 3/16* (2013.01); *A61B 3/165* (2013.01)

(58) Field of Classification Search
CPC ....... A61B 3/00; A61B 3/0008; A61B 3/0091; A61B 3/02; A61B 3/028; A61B 3/10
(Continued)

(56) References Cited

U.S. PATENT DOCUMENTS 3,756,073 A 9/1973 Lavallee et al.
5,442,412 A * 8/1995 Frey ...................... A61B 3/113
351/208

(Continued)

FOREIGN PATENT DOCUMENTS

CN 1518948 A 8/2004
CN 1646062 A 7/2005

(Continued)

OTHER PUBLICATIONS

English language Search Report issued by the State Intellectual Property Office of People's Republic China in relation to Chinese Application No. 201480046193.2 dated Mar. 10, 2017 (3 pages).

(Continued)

*Primary Examiner* — Robert E Tallman
(74) *Attorney, Agent, or Firm* — Robert P. Michal, Esq.; Carter, DeLuca, Farrell & Schmidt, LLP

(57) ABSTRACT

An optometric instrument includes an alignment device that includes light sources for sending out light beams through one or more light channels from the instrument onto the retina of an eye of a patient. The light channels are directed parallel with the visual axis of the eye at correct alignment, whereat the light beams are visible for the patient in an intended way. A method for aligning an optometric instrument includes sending out light beams from the light sources through one or more light channels onto the retina of the eye of a patient, and positioning the instrument to have the light channels parallel with the visual axis of the eye of the patient as a result of finding a position, wherein the light can be correctly viewed by the patient.

23 Claims, 8 Drawing Sheets

Figure 1B:
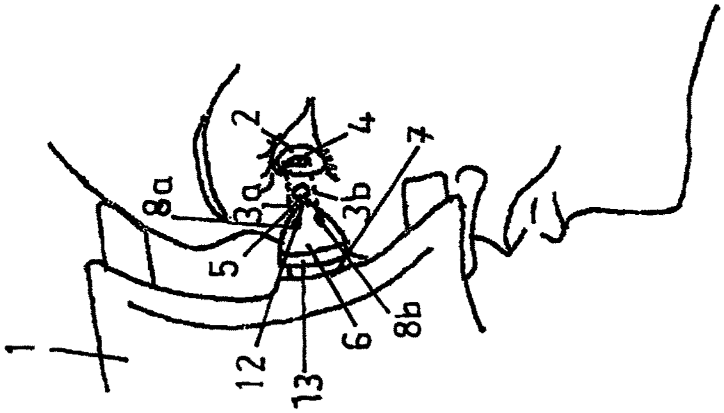

(51) Int. Cl.
*A61B 3/15* (2006.01)
*A61B 3/16* (2006.01)

(58) Field of Classification Search
USPC ................................ 351/200, 205, 206, 246
See application file for complete search history.

(56) References Cited

U.S. PATENT DOCUMENTS

| | | | |
|---|---|---|---|
| 5,546,941 A | 8/1996 | Zeimer et al. | |
| 5,708,494 A | 1/1998 | Iijima et al. | |
| 5,793,468 A | 8/1998 | Shalon et al. | |
| 5,909,271 A | 6/1999 | Maus et al. | |
| 6,131,574 A | 10/2000 | Kohayakawa | |
| 6,361,495 B1 * | 3/2002 | Grolman ................ | A61B 3/165 600/401 |
| 2002/0047990 A1 | 4/2002 | Fergason et al. | |
| 2003/0011745 A1 | 1/2003 | Molebny et al. | |
| 2003/0086060 A1 | 5/2003 | Beverly | |
| 2005/0117782 A1 | 6/2005 | Imaoka et al. | |
| 2007/0216909 A1 | 9/2007 | Everett et al. | |
| 2012/0203086 A1 | 8/2012 | Rorabaugh et al. | |
| 2012/0203239 A1 | 8/2012 | Vukich et al. | |

FOREIGN PATENT DOCUMENTS

| | | | |
|---|---|---|---|
| EP | 1121895 | A2 | 8/2001 |
| JP | S6458238 | A | 3/1989 |
| JP | 2002034928 | A | 2/2002 |
| WO | WO-2013/035091 | A1 | 3/2013 |

OTHER PUBLICATIONS

International Search Report issued by the European Patent Office acting as the International Searching Authority in relation to International Application No. PCT/FI2014/050500 dated Oct. 9, 2014 (3 pages).

Finnish Search Report issued by the Finnish Patent and Registration Office in relation to Finnish Patent Application No. 20135876 dated May 14, 2014 (2 pages).

* cited by examiner

OPTOMETRIC INSTRUMENT WITH ALIGNMENT MEANS AND METHOD FOR ALIGNING AN OPTOMETRIC INSTRUMENT

CROSS-REFERENCE TO RELATED APPLICATIONS

The present application is a Continuation of PCT Application No. PCT/FI2014/050500 filed Jun. 19, 2014 which claims priority from Finnish Patent Application Serial No. 20135684 filed Jun. 20, 2013 and Finnish Patent Application Serial No. 20135876 filed Aug. 30, 2013, the entire disclosure of each of which is incorporated by reference herein.

TECHNICAL FIELD

An optometric instrument with alignment means and a method for aligning an optometric instrument.

BACKGROUND

Most optometric and ophthalmic procedures, such as retinal examinations, tonometry and eye surgery, require accurate aligning of the instrument being used in them.

Known alignment methods are usually based on illumination of the eye followed by detecting the back-scattered light or by imaging the eye. AU patent 2006246323B2 is an example of the former solution and JP patents 0330841662 and 050245262, EP patent 254002B1 and CN patent 102551654 of the latter one.

Some alignment methods are meant to be performed either by the patient himself or as a result of feedback information from the patient. Such self-alignment methods are especially used in hand-held tonometers for measuring eye-pressure, for which EP Even these self-alignment methods, however, are based on imaging the eye, and they are not user-friendly enough to be used in instruments for home use.

U.S. Pat. No. 5,442,412 discloses a patient responsive eye fixation target method. The device to perform the method is based on a sensor that detects eye movement and notifies the patient of an erroneous eye position with a requirement to change it. The device has two light sources that produce a dot and a circle, respectively, to be seen by the patient for helping the patient to return the correct eye position. The device supplies an eye movement error signal to one of the second light sources to adjust the dot's appearance for guiding the patient in the realignment.

This quite complicated solution is intended for a great variety of ophthalmic procedures, laser surgery included.

There is therefore a need for a simple alignment method that reliably could be performed by the patient himself with instruments for home use without problems.

OBJECTS AND SUMMARY

One object of the invention is an optometric instrument especially for home use, wherein the alignment easily can be adjusted by the patient himself.

Another object of the invention is an optometric instrument, wherein the alignment easily can be adjusted by the doctor or other measurer in cooperation with or without the aid of the patient.

The invention is realized by means of an optometric instrument with alignment means. The instrument comprises a support inside which there is a measurement probe and one or more light channels, light sources on or in the support positioned on the basis of the size of the pupil for sending out light through one or more light channels from the instrument via the support and out onto the retina of the eye of a patient. The light channel(s) are directed parallel with the visual axis of the eye at correct alignment, whereat the light beams are visible for the user in an intended way.

The invention is also concerned with a method for aligning an optometric instrument that comprises a support inside which there is a measurement probe, one or more light channels being arranged on the basis of the size of the pupil, and light sources positioned for sending out light through said one or more light channels from the instrument via the support and out onto the retina of the eye of a patient, the light sources being on or in the support. The method comprises the steps of sending out light beams from the light sources through said one or more light channels onto the eye of a patient, and positioning the instrument to have the light channels parallel with the visual axis of the eye of the patient as a result of finding a position, wherein the light can be correctly viewed by the user.

At correct alignment, when the light or light beams are visible, the alignment can, depending on embodiment, be performed either by the patient or a doctor performing the alignment (and the measurement to be done with the instrument) or by both the patient and the doctor in an intended way.

The technology of the invention can thus be used for constructing instruments either for self-alignment (and self-measurement) by the patient or for an alignment (and measurement) to be performed by another person, like a doctor.

In the versatile embodiments of the invention, these functions are combined so that the alignment can be performed alternatively either by the patient or by the other person alone or by both of them separately or in cooperation.

The term doctor is in this text meant to cover any possible other person than the patient that aligns the instrument and performs the measurement.

The term user is in this text meant to cover any possible person that aligns the instrument and performs the measurement, such as the doctor or the patient himself.

The term patient is in this text meant to cover a person for which the alignment and/or measurement is performed. The patient can also be the person that aligns the instrument himself and/or performs the measurement himself alone or in co-operation with the doctor.

When, the positioning (alignment) of the instrument is performed by the patient himself for e.g. self-measurement, the patient is directly guided by the visibility of the light sent out via the cornea and further to the retina of the eye. The idea lies in the fact that if the instrument is not correctly aligned, the patient cannot see the light at all or he cannot see it in the intended way or he can see it only partly.

When, the positioning of the instrument is performed by a doctor, the doctor is guided by the visibility of the light sent out and reflected from the cornea of the eye of the patient. Analogously, the idea lies in the fact that if the instrument is not correctly aligned, the doctor cannot see the light at all or he cannot see it in the intended way or he can see it only partly.

The preferable embodiments of the inventions have the characteristics of the sub-claims.

There are several different ways to construct the light channels extending through the support from the end facing the instrument and to the other end that is against the eye.

The instrument of the invention can for instance have light channels to be directed to the eye, which are lightened from the other end of the support by means of e.g. Light-Emitting-Diodes (LEDs) to be used as light sources.

When the optometric instrument is an ophthalmic device having a measurement probe and a surrounding tip, around which probe and tip there is a support, the light channels can be positioned on or in the support. In such a solution, the light sources are positioned at the instrument end of the light channels (said end of the support facing the instrument) to send light from the instrument end into the inside of the support and out from the other end to hit the retina via the cornea of the eye of the patient.

The front side of the instrument is in this text the side that is against the patient's face, whereas the back side of the instrument is the other side of the instrument (being against the face of the doctor in case there is a doctor).

The light channels can in some embodiments consist of separate light channels showing the light as light beams to be seen by the patient as points of light upon correct alignment when looking at them from the front side of the instrument. When a doctor performs the alignment, he looks, from the back side of the instrument, at reflected points of light. The points of light are in this case reflected from the cornea of the eye of the patient. Optionally, the light channels can be grouped in special constellations with respect to each other so that the points of light form different patterns, such as geometric figures, like circles, triangles, quadrats or ovals. There can even be one single light channel forming a single point or a shape of light to be seen.

In an embodiment with e.g. four light channels, the user (patient or doctor) sees four points of light when he places the device to measure e.g. the intraocular pressure. The points can be sharp or fuzzy depending on the focus point, i.e whether the person is long- (or far-) sighted, near- (or short-) sighted or something there between and can or cannot see the points being sharp at the distance used. If the instrument, such as an ophthalmic device, is not aligned, the points cannot be seen or they can be seen only partly. If the device is in an angle within a certain area to the visual field or it is not on the middle of it, only a part of the points can be seen. If the angle to the visual field is outside a certain value, the points cannot be seen at all.

The light channels are preferably arranged so that the distance between the points are determined on the basis of the size of the pupil, preferably corresponding to the size of the pupil i.e. ca 5 mm. If the mutual distance of the points is too long, the invention does not work in the intended way, since then the light would not hit the retina via the cornea of the eye of the patient as it should.

Implementations of light channels in or on the support that give rise to points of light can be realized e.g. by means of small tubes or hollow spaces inside the support or openings on the surface of the support inside which the light proceeds.

An alignment by using light channels defined by openings giving rise to points of light to be seen by the patient or the doctor can alternatively be realized by means of a hollow support or a non-hollow (i.e. compact) support of diffusive material to be lightened with the light sources instead of using tubes or hollow spaces inside which the light proceeds.

A diffusive material can e.g. be glass or plastic and enables light to travel through it even if it does not allow people see through it. Diffusive (also called diffusion or diffused) glass or diffusive plastic (such as frosted glass produced by the sandblasting or acid etching of clear sheet glass) is used e.g. in applications for evenly distributing light across its surface area. Frosted refers to the appearance of the surface after etching, which is no longer transparent, but frosty in appearance.

In such an implementation, the hollow or compact support of the probe is coated with non-transparent material by having one or more openings in the coating or leaving corresponding areas uncoated. Instead of a coating, the support can have some other kind of non-transparent surface material with one or more openings or uncoated areas in the same way.

In such a support, which is hollow or consists of diffusive material with a coating or surface material, the light channels can consist of said uncoated areas (or "openings") in the coating or surface material allowing the light or light beams from the light sources to pass out from the support. The uncoated areas can thus instead of openings be of diffusive [or photo-conducting] material.

The uncoated areas can be arranged in different ways.

They can be openings being situated in relation to each other so that points of lights can be seen in the same way as in the embodiment with the light channels that consisted of small tubes or hollow spaces as mentioned above. Depending on their position on the surface of the support, different constellations are possible.

The points of light to be seen can be a result of point-like uncoated areas of diffusive material in the surface material of the support.

In an embodiment with the support itself being of diffusive material, the most preferable form or pattern for the uncoated area or opening is, however, a ring, of practical reasons. This is because an incorrect alignment is found to be easiest to recognize by the patient if the correct an intended form or pattern of light to be seen is designed in the form of a ring. In this embodiment, wherein, the support is of diffusive material, distortions and deformations from a correct visual view of the light to be seen gives a better difference to the correct view than in the case with a view of points of light.

Other geometric forms are possible but a ring, or circle, is an advantageous embodiment since it provides the easiest way to sense a wrong position of the light to be seen.

One possibility is to make an uncoated area or opening of a corresponding geometric form in the coating or surface material of the support, when the support is hollow, or is of diffusive material. A correct geometric form can be seen by the patient at correct alignment when the visual axis of the eye is parallel with the axis of the light channel when the support is lightened by the light sources.

There are further ways to design the view of light to be seen in the form of one or more rings or other continuous geometric forms.

Light channels that give rise to continuous geometric forms to be seen by the patient can be realized by means of corresponding forms on the light channels inside the support, or in a non-hollow or compact piece within the support with corresponding hollow spaces for the light.

The geometric form of the support prevents the light to proceed to the retina of the eye through the cornea when the instrument is inclined and not aligned, i.e. the direction of light is not parallel with the visual axis of the eye. When the light channel is formed as a geometric shape, like a ring, its size is designed on the basis of the size of the pupil, preferably corresponding to the size of the pupil, i.e. ca 5 mm, so that the light would hot the retina and go via the cornea.

In embodiments, wherein the form (or pattern) of light to be seen is a ring, there should be a sufficient number of light sources placed and distributed to enlighten the channels so that the ring would be uniform. In one possible useful embodiment to achieve the ring of light, there are for example six light sources evenly attached behind the light channels.

The support can be of any form that works in the mentioned intended way. One preferable embodiment is a cup-like support having a curved surface, since such a form works best in the intended way with respect to how the points of light are seen at alignment but seen differently or not at all when the instrument is not aligned.

There are different such geometric forms for the cup-like tip support to have, the preferred ones being the half of an ellipsoid (also called "spheroid"), a half sphere (also called "half globe" or "half ball"), an elliptic paraboloid, which is shaped like an oval cup, a circular paraboloid (being a special case of elliptic paraboloid), one of the sheet of a hyperboloid of two sheets, a conical surface or a half of a conical surface (a nappe).

The embodiment using a cup-like support also can work in some pyramid or cone form of which there are different types and dimensions.

All these different forms mentioned are meant to be covered by the term "cup-like".

Of all the different embodiments mentioned, the most useful solution, especially in the case, wherein the alignment is performed by a doctor, is considered to be an instrument, wherein diffusive material is used to form the light channels and the light to be seen by the user has the form of a ring or other continuous geometric shape. However, also the embodiment using points of light can be used in all embodiments. The patient and/or the doctor can then see the light from one or more light sources in the form of a ring when the instrument is aligned. When, the positioning and alignment of the instrument is performed by a doctor, the doctor is guided by the visibility of the light beams sent out and reflected from the cornea of the eye of the patient.

Naturally the horizontal position of the instrument or device with respect to the eye of the patient has to be correct, which takes place when the patient is looking into the device and there is therefore no need for any technical adjustment in that respect.

In a correct alignment of the instrument or device, as provided by the invention, i.e. when the light sent out hits the retina through the cornea, the light channels are directed parallel with the visual axis of the eye.

In addition, the inclination of the instrument or device has to be correct, which takes place when the instrument or device is straight. An advantageous embodiment of the invention provides a solution for adjusting the inclination as well.

Therefore, in one possible advantageous embodiment, the instrument might have means for measuring the inclination of it, like an inclinometer or clinometer.

An inclinometer or clinometer is an instrument for measuring angles of slope (or tilt), elevation or depression of an object with respect to gravity. It is also known as a tilt meter, tilt indicator, slope alert, slope gauge, slope indicator, gradient meter, gradiometer, level gauge, level meter, declinometer, inclinometer, clinometer or pitch & roll indicator. Clinometers measure both inclines (positive slopes, as seen by an observer looking upwards) and declines (negative slopes, as seen by an observer looking downward) using three different units of measure: degrees, percent, and topo.

In this advantageous embodiment, especially to be used for a doctor-performed alignment, wherein an inclinometer or the like is used, the light sources of the instrument are of different colors, preferably Light Emitting Diodes (LEDs) sending out green or red light.

A light source sending out green light is in this text called a green light source and a light source sending out red light is in this text called a red light source.

A useful solution is to use three green light sources and three red light sources suitable positioned at the instrument so that a uniform ring of light appears when the light sources are on.

A control system in the instrument turns the green light sources on and shuts the red light sources automatically on the basis of a signal from the inclinometer when the instrument is straight and analogously turns the red light sources on and shuts the green light sources automatically on the basis of a signal from the inclinometer when the instrument is not straight.

The doctor can then see a green ring reflected from the retina of the patient when the instrument or device is straight, i.e. it has the correct straight inclination and the measurement probe is directed correctly to the cornea with the visual axis parallel with the light channels.

If the doctor can see a red ring (reflected from the retina of the patient) it means that the measurement probe of the instrument is directed correctly to the cornea with the visual axis parallel with the light channels but the instrument or device is not straight, i.e. it has an incorrect inclination. This might e.g. takes place when a patient is looking up or down (instead of keeping the head still and straight) whereby the instrument or device will be inclined as well. The position of the head can then be corrected so that the doctor can see a green ring.

If no light (ring or other pattern) can be seen at all or it can be seen only partly, the instrument is neither correctly in line with (parallel with) the visual axis of the eye, and nor is it straight.

Instead of having red and green light sources to be turned on or off dependently on the inclination of the instrument, other color pairs or combination of several colours can be used for indication of the inclination. Using red and green light is, however, a pleasant choice of colors, since they traditionally indicate stop and go functions, respectively.

The invention is useful in all kinds of optometric devices and instruments, especially instruments devices for ophthalmic examinations including measurements related to the intraocular pressure and the thickness of cornea. The devices for the former examinations mentioned are often called tonometers.

The invention is very useful in a tonometer using rebound technology, wherein the intraocular pressure is measured on the basis of the movements of a one-time probe hitting the eye and bouncing back. In the rebound technology, it is extremely important that the measurement is made on the middle of the cornea. The primary aim of the invention is to facilitate the direction of a device made for users for home use.

The invention is especially intended for devices and instruments, wherein the patients make the measurements by themselves and is generally advantageous for small hand-held ophthalmic instruments that can be easily moved from one eye to the other. The simple, user friendly alignment not only eliminates human errors but also speeds up the measurement or examination process.

Next, the invention is further illustrated by means of some example embodiments by referring to figures. The invention is not restricted to the details of these examples.

FIGURES

Figure 1A:
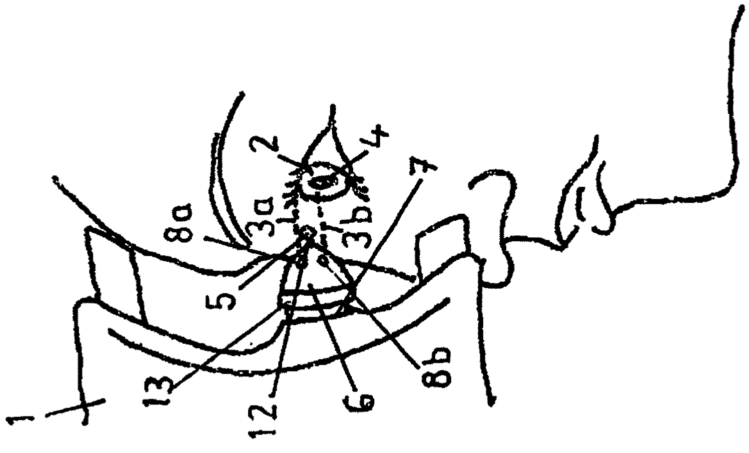

FIGS. 1*a* and 1*b* show the principle of a first embodiment of the alignment procedure of the instrument of the invention by directing light beams from the instrument on the eye of a patient.

Figure 2A:
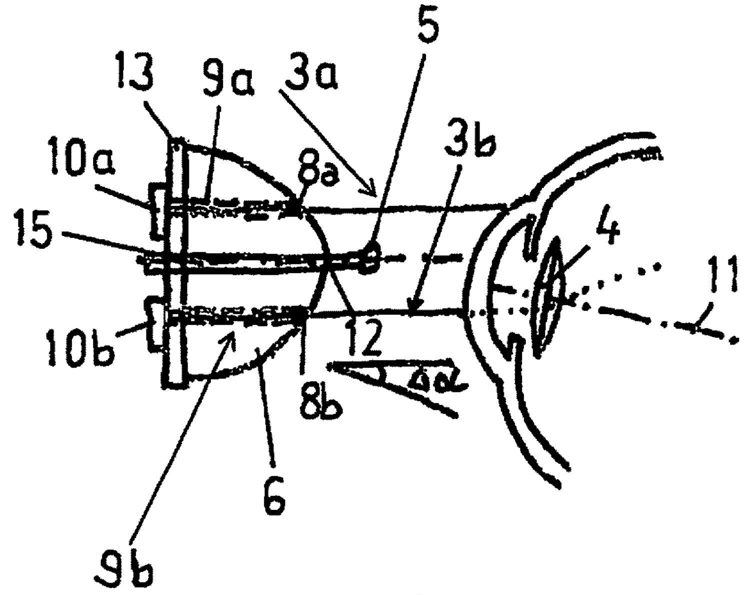
Figure 2B:
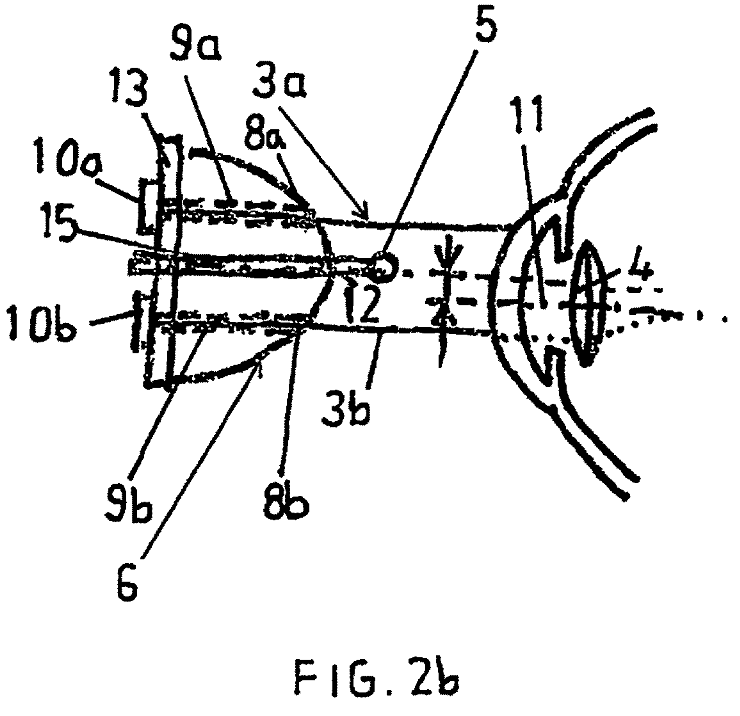
Figures 2C, 2D, 2E:
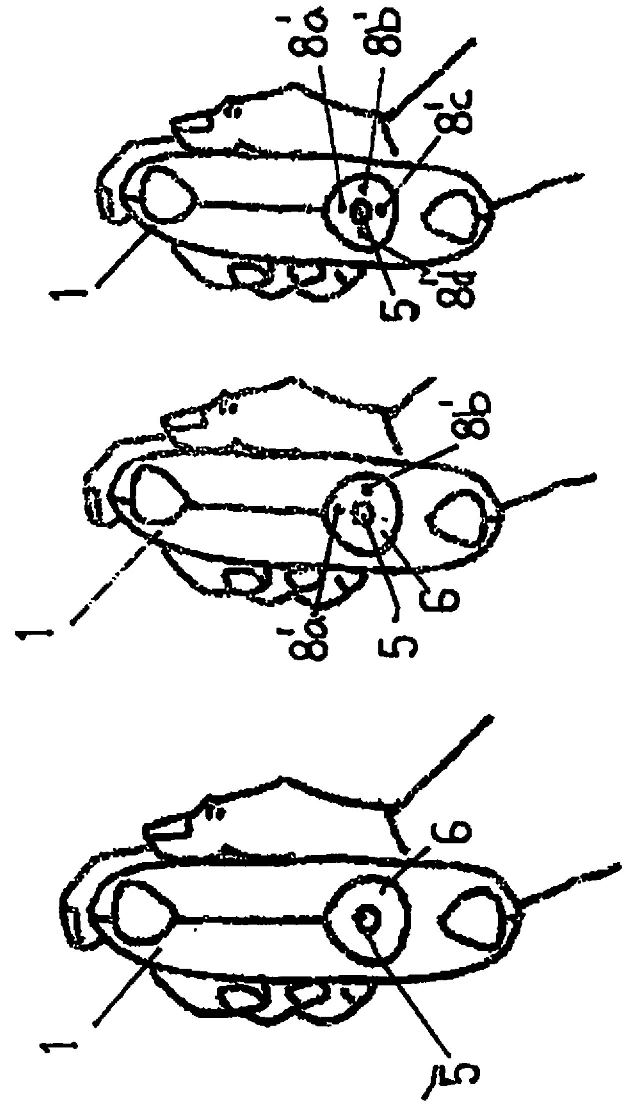
Figure 3F:
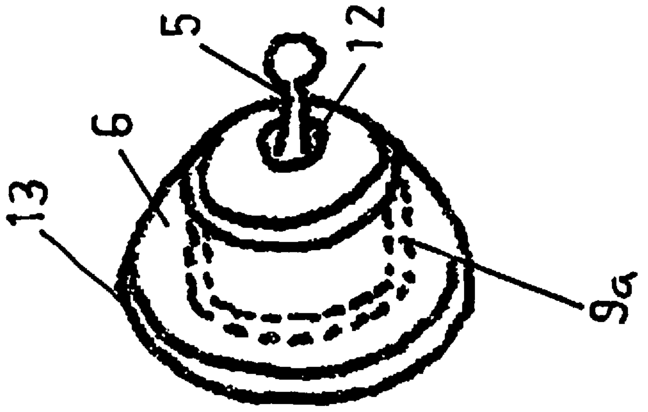
Figure 2F:
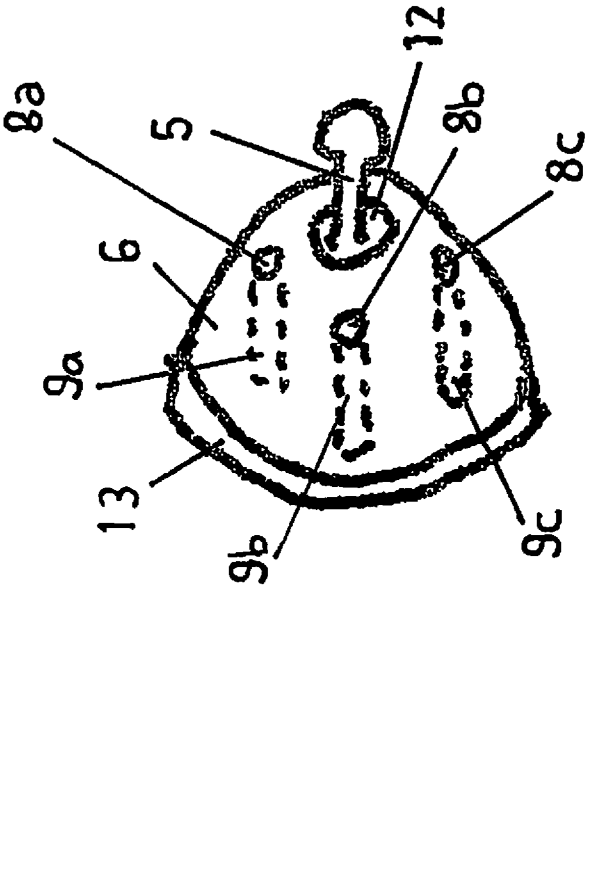
Figure 3A:
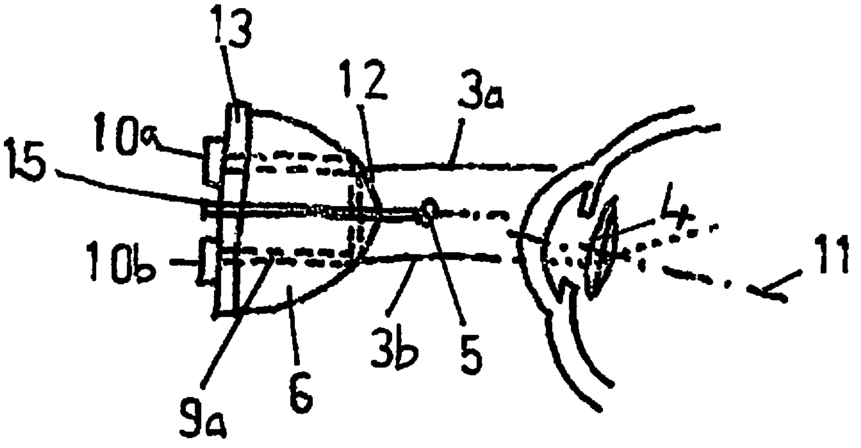
Figure 3B:
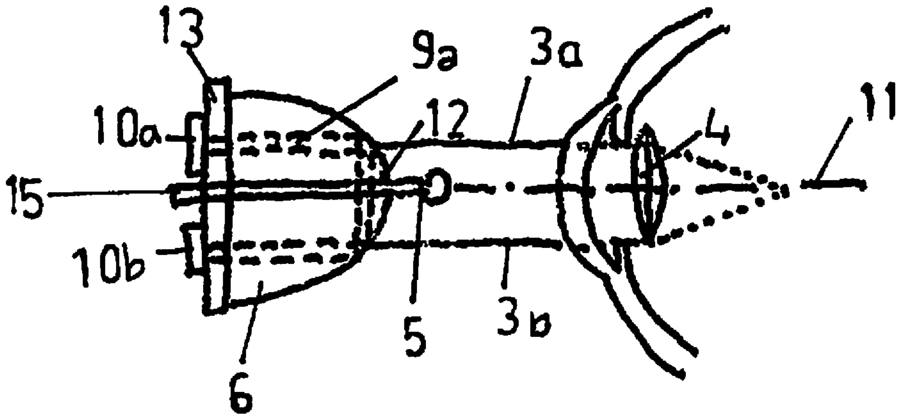
Figure 3E:
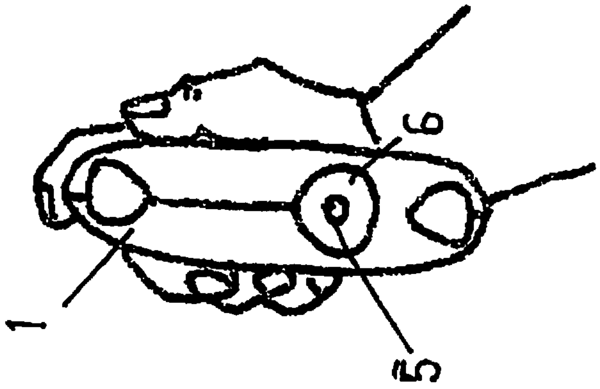
Figure 3D:
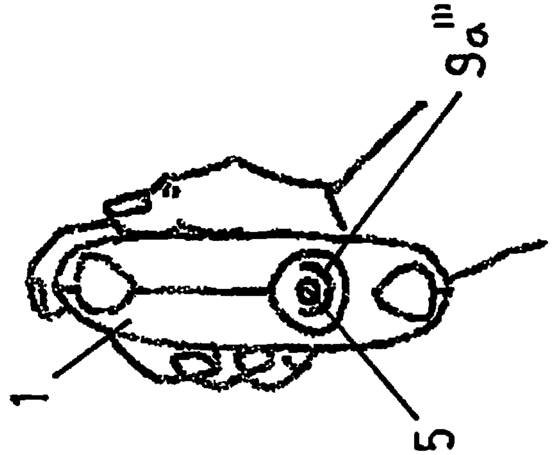
Figure 3C:
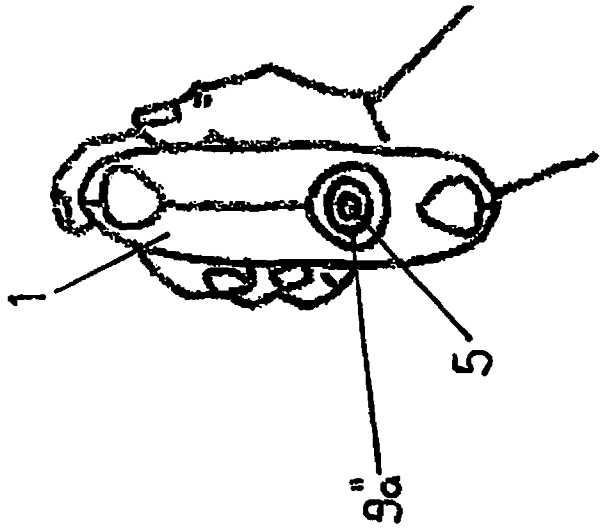
Figure 4A:
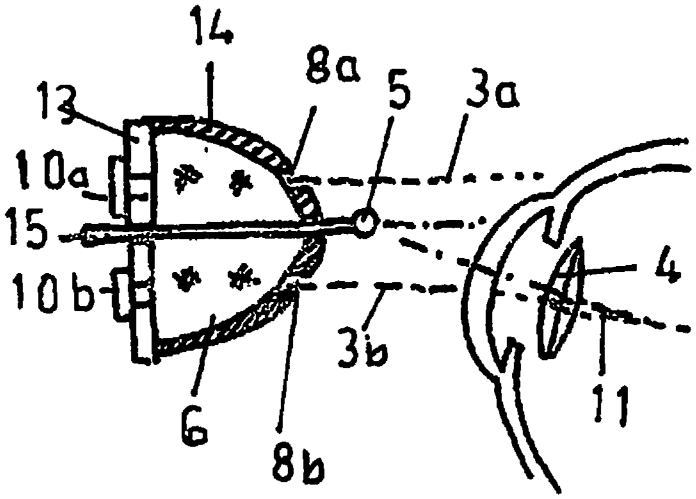
Figure 4B:
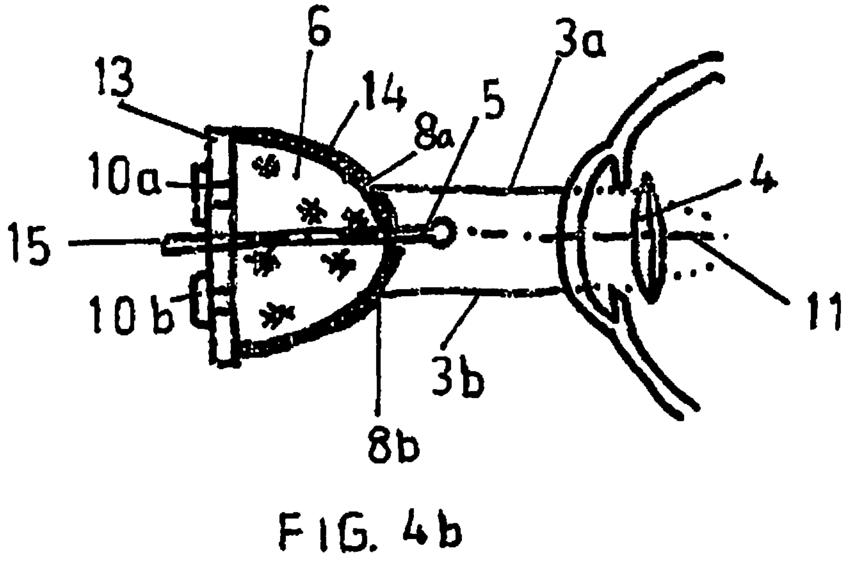
Figure 5B:
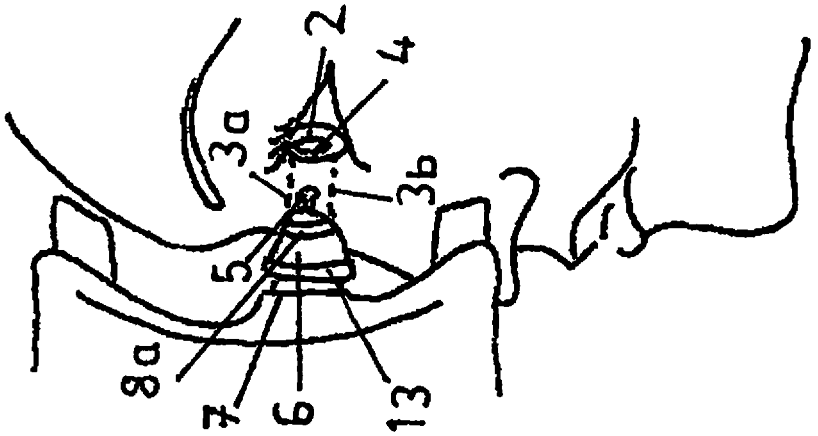
Figure 5A:
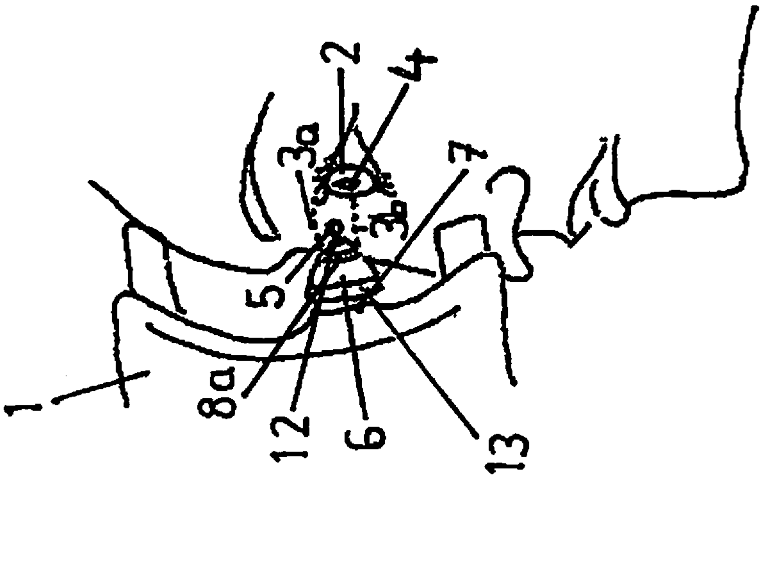

FIGS. 2*a*, 2*b*, 2*c*, 2*d*, 2*e* and 2*f* present schematically a first embodiment of the invention, FIGS. 3*a*, 3*b*, 3*c*, 3*d*, 3*e* and 3*f* present schematically a second embodiment of the invention, FIGS. 4*a* and 4*b* present schematically a third embodiment of the invention, and FIGS. 5*a* and 5*b* show the principle of a second embodiment of the alignment procedure of the instrument of the invention by directing light beams from the instrument on the retina.

DETAILED DESCRIPTION

FIGS. 1*a*-1*b* and 5*a*-5*b* show the principle of the alignment of the invention as implemented in an ophthalmic apparatus, which is a tonometer 1 and aligned to an eye 2 to be examined by means of directing light beams 3*a* and 3*b* on the retina 4. Two light beams 3*a* and 3*b* can be seen in the figure in order to make the illustration simpler. In a real solution, there are usually four light beams even if the invention also can work by using fewer or more light beams, even by using one single light beam.

In FIGS. 1*a* and 5*a*, the tonometer is not correctly aligned as the light beams 3*a* and 3*b* do not hit the retina 4 and the instrument is inclined.

In FIGS. 1*b* and 5*b*, the tonometer is correctly aligned as the light beams 3*a* and 3*b* hit the retina 4.

The tonometer 1 is close to the eye 2 and in it there is a probe 5, which is shot toward the eye, the intraocular pressure being calculated from the movements of the probe 5, or the variations in the movements. The movement is created in a conventional manner magnetically with the aid of coils inside the tonometer 1, which are not shown here, and of a rod/wire of magnetic material, which goes inside the coil. Of course there are other ways to create the movement and the way to perform it is outside the scope of this invention.

It is, however, important for the achieving of a correct result that the probe 5 approaches the eye 2 in the correct angle since the measurement is very sensitive for errors otherwise.

The probe 5 has a tip (here using the same reference number for the probe and its tip) on its end and is surrounded by a cup-like support 6 fastened to the outer frame 7 of the tonometer 1. In the support 6, there is a hollow space for a channel or space 15 (see FIGS. 2*a*, 2*b*, 2*f*, 3*a*, 3*b*, 3*f*, 4*a* and 4*b*) for the probe 5 to move through the support 6 and out from an opening 12 (see FIGS. 2*a*, 2*b*, 2*f*, 3*a*, 3*b*, 3*f*, 4*a* and 4*b*) in it. In a measurement situation, the probe 5 enters the eye through the opening 12 on the edge of the support 6.

In FIGS. 1*a* and 1*b*, showing a first embodiment of the invention, the support 6 also has small point-formed uncoated areas, spaces and/or openings 8*a*, 8*b* for light channels 9*a*, 9*b* (see FIGS. 2*a*, 2*b*, and 20 for transporting the light beams 3*a* and 3*b* or the light to be directed onto the retina 4 of the eye 2 to be seen as points of light by the patient.

In FIGS. 5*a* and 5*b*, showing a second embodiment of the invention, the support 6 has a ring-formed uncoated areas, space and/or opening 8*a* for light channels 9*a*, 9*b* (see FIGS. 3*a*, 3*b*, 3*f*, 4*a* and 4*b*) for transporting the light beams 3*a* and 3*b* or the light to be directed onto the retina 4 of the eye 2 to be seen as a ring of light by the patient.

FIGS. 2*a*-2*f* present schematically a first embodiment of the invention, wherein the light channels are formed by thin tubes 9*a* and 9*b* through which light beams illustrated by 3*a* and 3*b* proceed through openings 8*a* and 8*b* on the cup-like support 6. The opening 12 for the probe 5 can also be seen. Instead of being hollow tubes, the channels can consist of diffusive material.

When looking at the light channels 9*a* and 9*b* of the tonometer 1 from the front, the light channels 9*a* and 9*b* visually give rise to a pattern of points of light, which can be seen by the user when the tonometer is aligned. The light sources 10*a* and 10*b*, which preferably consist of Light-Emitting Diodes (LEDs), are placed at the instrument end of the light channels 8*a* and 8*b* (the end of the support facing the instrument). They are used to produce the light beams 3*a* and 3*b* to be transported through the light channels 9*a* and 9*b* and out therefrom to hit the retina 4. The support 6 is in FIGS. 2*a* and 2*b* connected to the instrument through an intermediate piece 13, to which the light sources 10*a* and 10*b* might be fastened. The way of connecting the light sources and the support 6 to the tonometer or to each other is known technique for one skilled in the art and not relevant for the invention itself. There can be another number of light sources than two. The important thing is just to install the light sources 10*a* and 10*b* so that they can produce the light to the support 6 or inside the light channels 9*a* and 9*b*. The light channels 9*a* and 9*b* are in FIGS. 2*a* and 2*b* placed inside the cup-like support 6.

In FIG. 2*a*, the patient (or user) is not looking straight to the probe 5 of the instrument, i.e. the tonometer 1, and the tonometer 1 is therefore not aligned. The visual axis 11 is not parallel with the light beams 3*a* and 3*b* because it forms an angle α to the light beams 3*a* and 3*b* (and to the movement direction of the probe 5). As a consequence, the user cannot see the points of light since the light beams 3*a* and 3*b* are not directed on the retina 4.

In FIG. 2*b*, the patient or user is looking straight to the probe 5 of the instrument, i.e. the tonometer 1, and the tonometer 1 is therefore aligned. The visual axis 11 is now parallel with the light beams 3*a* and 3*b* because the angle α to the light beams 3*a* and 3*b* is zero. The user can now see the points of light since the light beams 3*a* and 3*b* are directed perpendicular to the retina 4.

In FIG. 2*c*, the user can not see any points of light since the tonometer 1 is not aligned. The angle to the visual field is completely outside a scope within which any points of light could be seen and therefore, any points cannot be seen at all.

In FIG. 2*d*, a part of the points of light can be seen, even if the tonometer 1 is not correctly aligned. The alignment of the light beams 3*a* and 3*b* from the tonometer 1 is within the scope of the visual field even if not parallel and therefore only a part of the points 8*a*', 8*b*' of light can be seen. The points of light 8*a*', 8*b*' can be seen at the openings 8*a* and 8*b* on the cup-like support 6.

FIG. 2*e* is a view showing that all the points of light 8*a*', 8*b*', 8*c*' and 8*d*' (when having four light channels) are visible for the user when the tonometer 1 is aligned and the visual axis is parallel with the light beams 3*a* and 3*b*.

FIG. 2*f* is a partial view showing the cup-like tip support 6 with openings 8*a*, 8*b* and 8*c* for the light channels 9*a*, 9*b* and 9*c* and an opening 12 for the probe 5. The channels 9*a*, 9*b* and 9*c* are inside the support 6 and therefore drawn by dotted lines.

FIG. 3*a*-3*d* present schematically a second embodiment of the invention, wherein one light channels 9*a* is formed by means of a transparent inner ring-formed space throughout a non-transparent support 6, the transparent inner ring-formed space forming the light channel 9*a* through which the light proceeds as illustrated by FIGS. 3*a* and 3*b*. In FIGS. 3*a*-3*d* one ring is used, but if desired, several rings or several geometric forms can be used.

There are other possibilities to form a ring-formed channel (or some other geometric form). An example is to use a support described in FIGS. 4*a* and 4*b* and have the support made of diffuse material or by means of a hollow support having a non-transparent surface material and by leaving a part of the surface uncoated or without non-transparent material allowing the light to pass. If this part has the form of the ring, the user can see a ring of light when looking at the instrument from the front side as long as the instrument is aligned.

A further possibility is to make use of an extra body piece inside the support, by means of which or on which the channel or channels are formed.

If the light channel has the form of a cylinder like in FIGS. 3*a*-3*e*, the light channel 9*a* is ring-like from the patient's view when seen from the front. Thus, the light channel 9*a* gives rise to a ring of light to be seen by the patient. If using an extra body piece, the non-transparent part of the body piece and the transparent body peace can be manufactured separately and then connected together.

Like in FIG. 2*a*, there is the situation in FIG. 3*a* that the patient or user is not looking straight to the probe 5 of the instrument, i.e. the tonometer 1 and the tonometer 1 is therefore not aligned. The visual axis 11 of the eye is not parallel with the light beam 3*a* because it forms an angle α to the light beam 3*a*. As a consequence, the user can not see the ring of light (at least not completely) since the light beam 3*a* is not directed on the retina 4.

In FIG. 3*b*, the patient or user is looking straight to the probe 5 of the instrument, i.e. the tonometer 1, and the tonometer 1 is therefore aligned. The visual axis 11 is now parallel with the light beam 3*a* b because the angle α to the light beams 3*a* and 3*b* is zero. The user can now see the ring of light since the light beam 3*a* is directed perpendicular to the retina 4.

FIG. 3*c* is a view showing a ring 9*a*" of light visible for the user when the tonometer 1 is aligned and the visual axis is parallel with the light beam 3*a*.

In FIG. 3*d*, a part of the ring 9*a*'" of light can be seen, even if the tonometer 1 is not correctly aligned. The alignment of the light beam 3*a* from the tonometer 1 is within the scope of the visual field even if not parallel and therefore only a part of the ring of light can be seen. The ring of light can be seen at the light channel 9*a* in the cup-like support 6.

In FIG. 3*e*, the user can not see any ring of light at all since the tonometer 1 is not aligned. The angle to the visual field is completely outside a scope within which any light could be seen and therefore, the ring can not be seen at all. FIG. 3*e* is therefore the same as FIG. 2*c*.

FIG. 3*f* is a partial view showing the cup-like tip support 6 inside which there is a transparent inner space or part forming a light channel 9*a* through which the light beam can proceed. There is a space formed for the probe 5 as well within which it can move and an opening 12 from which it can come out from the support 6.

FIG. 4*a*-4*d* presents schematically a third embodiment of the invention, wherein the light channels 9 are formed by the openings 8*a* and 8*b* themselves on the support allowing points of light to be seen by the user as in the first embodiment of FIGS. 2*a*-2*d*.

As in this third embodiment, however, there are no tubes to form the light channels. The points by light to be seen by the user are instead a result of that the space inside the support 6 is lightened or if being compact and of diffusive material, the support 6 itself is lightened or illuminated with LEDs or other light sources 10*a* and 10*b*.

The support 6 of the probe 5 is in this case coated which non-transparent material by having one or more openings or uncoated areas in the coating 14.

If a support 6 with a non-transparent coating 14 is used, the support 6 is permeable for light only at the openings 8*a* and 8*b* (only two can be seen in the figure but there can be m more of them or only one) and therefore they form "channels" for the light to be transported out. The opening can preferably be a continuous ring around the surface of the support on such a place that its size corresponds to at least approximately the size of the pupil so that the light would hit the retina via the cornea. In that case there is only one opening 8*a*.

The material of the support 6 is selected so that the support 6 can act like a diffuser, i.e. it diffuses, spreads out or scatters light in a manner. The surface 14 of the diffuse support 6 that is used can be of or can be coated with a material impermeable for light but leaving the channels (or openings) uncoated. The geometry of the support 6 prevents the light beams to enter the retina when the device is inclined or is not parallel with the visual axis.

In FIG. 4*a*, the patient or user is not looking straight to the probe 5 of the instrument, i.e. the tonometer 1, and the tonometer is therefore not aligned. The visual axis 11 is not parallel with the light beams 3*a* and 3*b* or light beam because it forms an angle α to the light beams 3*a* and 3*b* or light beam. As a consequence, the user can not see the points of light or the ring of light since the light beams 3*a* and 3*b* are not directed on the retina 4.

In FIG. 4*b*, the patient or user is looking straight to the probe 5 of the instrument, i.e. the tonometer 1, and the tonometer 1 is therefore aligned. The visual axis 11 is now parallel with the light beams 3*a* and 3*b* because the angle α to the light beams 3*a* and 3*b* is zero. The user can now see the points of light since the light beams 3*a* and 3*b* are directed perpendicular to the retina 4.

If in the embodiment of FIGS. 4*a* and 4*b*, point-like openings 8*a* and 8*b* are used, then the visual views in the correct and incorrect alignment situations correspond to the situation in the first embodiment and are presented in FIGS. 2*c*-2*e*.

If in the embodiment of FIGS. 4*a* and 4*b*, a ring-like opening 8*a* and 8*b* are used, which is the preferred embodiment, then the visual views in the correct and incorrect alignment situations correspond to the situation in the second embodiment and are presented in FIGS. 3*c*-3*e*.

The invention claimed is:

1. An optometric instrument with alignment means, comprising:

a support including a measurement probe and one or more light channels, and light sources configured to send light through the one or more light channels and onto a retina of an eye of a patient, the light sources being on or in the support, wherein the one or more light channels are configured to transmit light in a direction parallel with the visual axis of the eye when the instrument is in correct alignment with the eye, wherein the light sources are configured to send light in the visible spectrum.

2. The optometric instrument of claim 1, wherein the one or more light channels includes separate light channels being grouped in a relation to each other for showing points of light to be seen by the patient upon correct alignment of the instrument.

3. The optometric instrument of claim 1 wherein the one or more light channels are in such a relation to each other that their mutual distance corresponds to the size of the pupil and a lens of the eye of the patient.

4. The optometric instrument of claim 2, wherein the one or more light channels are in such a relation to each other that the points of light form a geometric figure, comprising one of a point, a circle, a quadrangle, a triangle, an ellipse and a line.

5. The optometric instrument of claim 1, wherein the light sources are positioned to send the light beams into the inside of the support.

6. The optometric instrument of claim 1, wherein the light sources are Light-Emitting-Diodes (LEDs).

7. The optometric instrument of claim 1, wherein the light sources are configured to send light of at least two different colors.

8. The optometric instrument of claim 7, further comprising:

an inclinator for detecting the angle of slope of the instrument as inclination information, a transmitter in the inclinator for sending a signal with information of the inclination to a control system, and a control system which turns on and off the light sources of selected color of light on the basis of the inclination information received.

9. The optometric instrument of claim 3, wherein said one or more light channels are in such a relation to each other that the points of light form a geometric figure, comprising one of a point, a circle, a quadrangle, a triangle, an ellipse and a line.

10. The optometric instrument of claim 1 further comprising a surrounding support with a space for the movement of the measurement probe, the light channels positioned on or within the surrounding support.

11. The optometric instrument of claim 10, wherein the light channels comprise hollow spaces or tubes inside the support extending throughout the support.

12. The optometric instrument of claim 11, wherein the light channels comprise diffusive material extending throughout the support.

13. The optometric instrument of claim 10, wherein the support comprises a diffusive material.

14. The optometric instrument of claim 10, wherein the support is hollow.

15. The optometric instrument of claim 14, wherein the support is coated with a non-transparent material, the support having uncoated areas on the surface that form the light channels allowing the light beams from the light sources to pass.

16. The optometric instrument of claim 15, wherein the uncoated areas are openings for light channels.

17. The optometric instrument of claim 10, wherein the support includes a cup-like curved surface connected directly or via a connecting piece to the frame of the instrument.

18. The optometric instrument of claim 17, wherein the form of the support with its cup-like curved surface prevents the light to proceed to the retina of the eye when the optometric instrument is not aligned when the direction of the light beams is not parallel with the visual axis of the eye.

19. The optometric instrument of claim 15, wherein the uncoated areas are point-like and grouped in a relation to each other for showing points of light to be seen by the patient upon correct alignment.

20. The optometric instrument of claim 15, wherein the uncoated area has a continuous geometric shape.

21. The optometric instrument of claim 20, wherein the uncoated area has the form of a ring.

22. The optometric instrument of claim 20, wherein the size of the geometric shape corresponds to the size of the pupil.

23. The optometric instrument of claim 14, wherein the support is coated with a non-transparent material, the support having uncoated areas on the surface that form the light channels allowing the light beams from the light sources to pass.

* * * * *